United States Patent [19]

Gibson, III et al.

[11] Patent Number: 5,082,782
[45] Date of Patent: Jan. 21, 1992

[54] PRODUCTION OF HORSESHOE CRAB AMEBOCYTES IN VITRO

[75] Inventors: Daniel G. Gibson, III, Teaticket; Joan B. Hilly, Uxbridge, both of Mass.

[73] Assignee: Worcester Polytechnic Institute, Worcester, Mass.

[21] Appl. No.: 290,160

[22] Filed: Dec. 27, 1988

[51] Int. Cl.$^5$ ............................................. C12N 5/00
[52] U.S. Cl. ........................... 435/240.2; 435/240.1; 435/240.21
[58] Field of Search ............. 435/240.2, 240.21, 240.3, 435/240.31, 240.1, 1

[56] References Cited

U.S. PATENT DOCUMENTS 4,229,541  10/1980  Pearson ............................. 435/241

OTHER PUBLICATIONS

Armstrong, J. Cell Sci. 37: 169-180 (1979).
Armstrong, In "Biomed. Applic. of the Horseshoe Crab (Limulidae)", pp. 73-92, (1979).
Levin, In "Biomed. Applic. of the Horseshoe Crab (Limulidae)", pp. 131-146 (1979).
Pearson et al., In "Biomed. Applic. of the Horseshoe Crab (Limulidae)", pp. 93-102 (1979).
Ornberg et al., In "Biomed. Applic. of the Horseshoe Crab (Limulidae)", pp. 125-130 (1979).

Primary Examiner—Elizabeth C. Weimar
Assistant Examiner—Jasemine C. Chambers
Attorney, Agent, or Firm—Kilpatrick & Cody

[57] ABSTRACT

A method for producing horseshoe crab amebocytes in vitro by isolating amebocyte producing tissue from the gill flaps of horseshoe crabs, especially Limulus polyphemus. In contrast to all previous attempts to isolate and culture amebocytes from Limulus for the production of pyrogen-sensitive lysate, an effective method and means has been developed utilizing the discovery that the gill flaps are the source of the cells which differentiate into competent amebocytes. Once isolated, the tissue can be cultured long term in vitro on an artificial surface or as part of the gill flap leaflets, opened along one edge to allow access of the media to the developing amebocytes. Amebocytes are removed from the gill flaps by pulsing with Limulus serum, copper sulfate, detergent, or combinations thereof.

4 Claims, 1 Drawing Sheet

PRODUCTION OF HORSESHOE CRAB AMEBOCYTES IN VITRO

BACKGROUND OF THE INVENTION

There are four known species of horseshoe crabs, *Limulus polyphemus, Tachypleus tridentatus, Tachypleus gigas,* and *Carcinoscorpius rotundicauda*. The amebocyte is the only, or predominant, type of circulating cell in the blood of the horseshoe crab. The amebocyte is a nucleated cell having densely packed granules which contain endotoxin-sensitive clotting factors. Armstrong, in *Biomedical Applications of the Horseshoe Crab (Limulidae)*, pages 73-93 (Alan R. Liss, Inc., New York, N.Y. 1979), describes the details of the active pseudopod-directed motility of *Limulus polyphemus* amebocyte migrating in vitro on glass microscope coverslips and in vivo in gill leaflets isolated from young animals. Although the important role of the amebocyte in the coagulation of the blood of Limulus has been known for many years, it was only recently established that the elements required for coagulation: a serine esterase of 150,000 apparent molecular weight requiring both $Ca^{2+}$ and endotoxin for activation, and a clottable protein of 23,000-27,000 apparent molecular weight, are all intracellular.

The reaction between lysates of amebocytes and bacterial endotoxin provides the basis for the most sensitive currently available in vitro assay for endotoxin. Studies of hemolymph coagulation in the horseshoe crab, *Limulus polyphemus*, establish that the circulating blood cells, the amebocytes, secrete the blood clotting factors in response to bacterial endotoxins. Minute quantities of endotoxin cause amebocytes to aggregate and degranulate concomitant to clot formation, as described by Bang, *Bull. Johns Hopkins Hosp.* 98,325 (1956); and Levin and Bang, Bull. John Hopkins Hosp. 115, 337 (1964). All of the clotting proteins released by the amebocytes are contained within the numerous large granules filling the cytoplasm, as reported by Murer, et al., *J. Cellular Physiol* 86, 533 (1975). Bang reported an increase in free granules in the lymph of endotoxin injected crabs implying that stimulated amebocytes simply rupture (Bang, 1955). Dumont, et al., *J. Morphol* 119, 181 (1966) examined the ultrastructural changes of stimulated amebocytes and suggested that the granule membrane fused with the plasmalemma during release. Ornberg and Reese, pp. 125-130 in Biomedical Applications of the Horseshoe Crab Dec. 8 (1979), using a quick-freeze method, captured the membrane fusion in electron micrographs, demonstrating that this was the mechanism for release.

Although the production and application of the Limulus Amebocyte Lysate (LAL) test has become more standardized in recent years, significant variation occurs in lysate produced by different manufacturers and even from lot-to-lot within material produced by individual manufacturers. The successful cultivation of Limulus amebocytes in the laboratory would enable production of a lysate that is not subject to the variability of the natural environment. Such a standardized production would most probably reduce batch variability and seasonal variability of lysate.

In vitro cultivation of amebocytes might also eliminate or decrease the need to bleed horseshoe crabs so that the collection, transportation and possible depletion of the horseshoe crab population would not be necessary. Although the U.S. horseshoe crab population appears to be stable and in good numbers at this time, their number could easily be diminished by overutilization, as well as by diminished and deteriorating habitat. Unlike the American horseshoe crab which has apparently coped with twentieth century habitat and survived the challenge from the fertilizer, fishing and medical industries, its Japanese counterpart has not been so fortunate. As noted by Niwa, et al., *Jap. J. Med. Sci. Biol.,* 27, 108 (1974), as quoted in Shishikura, et al., *Biomedical Applications of the Horseshoe Crab* (Limulidae), p 185-201 (Alan R Liss, Inc., N.Y., N.Y. 1979), the Japanese horseshoe crab is an "endangered species and seemingly on its way to extinction due to reclamations and contamination".

Although Limulus appears to be extremely resilient to being bled from the collection of amebocytes, the impact of bleeding activity on the horseshoe crab population has not been clearly documented in the literature. Proposed rules which wee released in the Federal Register on Aug. 11, 1978 underscore the potential problem by requesting manufacturers of LAL to guarantee that the production of LAL will not have an adverse impact on existing crab populations and that horseshoe crabs will be returned alive to their natural environment after a single collection of their blood.

Interest in the laboratory cultivation of Limulus cells and tissues is not new. As early as 1959, when cell culture was still emerging from its infancy, Sanborn and workers reported in *Biol. Bull.* 117, 399, on the successful in vitro cultivation of a number of cell types, other than amebocytes, from Limulus tissues. These included primary explants of ovary, hepatopancreas, nerve, leg and cardiac muscle, all of which were cultivated by use of a simple hanging drop method. Although the medium employed in this study was not named, it contained inorganic salts, multiple sugars and organic acids all of which are consistent with contemporary cell culture media, and five to ten percent sterile Limulus serus. Cells were maintained up to thirty days, with vacuolation and granulation becoming pronounced after ten days.

Pearson and Woodland reported in *Biomedical Applications of the Horseshoe Crab* (Limulidae), 93-102 (alan R. Liss, Inc., New York, N.Y. 1979), that the general morphology of cells cultivated from Limulus primary explants are not unlike those encountered in explants of vertebrate tissue. They selected and tested a number of common cell culture media for their potential use in the cultivation of Limulus amebocytes: Minimal Essential Medium (MEM), Leibovitz (L-15), Medium 199 and Grace's Insect Medium (GIM). Lysate preparations from cultured amebocytes were tested for potency by using graded endotoxin solutions ranging from 0.1 ng to 1000 ng per ml. Since solid clots were not formed by lysate preparations, a graded endpoint was used ranging from 0 (negative) to +3 (a clot that would run when the tube was tilted 180°). Intermediate values wee based on degree of opacity, viscosity and production of floccules. None of the lysate preparations from amebocytes grown in vitro gave more than slightly positive results (+1 reaction) in the presence of 1000 ng of endotoxin. In U.S. Pat. No. 4,229,541 to Pearson disclosed a method for cultivating amebocytes in culture. However, although the results demonstrate that the amebocytes replicated in culture, it is now well known that mature amebocytes do not replicate. No source for new amebocytes has been described by Pearson or anyone else.

It is therefore an object of the present invention to provide a method and means to provide and for culturing amebocyte-producing tissue from horseshoe crabs in vitro.

It is a further object to provide a method and means for producing pyrogen-sensitive horseshoe crab lysate in large quantity by in vitro production of amebocytes.

It is a still further object of the present invention to provide a method and means for producing pyrogen-sensitive *Limulus polyphemus* lysate which is not dependent on harvesting of wild *Limulus polyphemus*.

SUMMARY OF THE INVENTION

A method for producing horseshoe crab amebocytes in vitro by isolating amebocyte producing tissue from the gill flaps of horshoe crabs, especially *Limulus polyphemus*. In contrast to all previous attempts to isolate and culture amebocytes from Limulus for the production of pyrogen-sensitive lysate, an effective method and means has been developed utilizing the discovery that tissue in the gill flaps is the source of the cells which differentiate into competent amebocytes. Once isolated, the tissues can be cultured long term in vitro unattached on an artificial surface, or as part of the gill flap leaflets, opened along one edge to allow access of the media to the developing amebocytes. Amebocytes are removed from the gill flaps by pulsing with Limulus serum, copper sulfate, detergent, or combinations thereof.

DETAILED DESCRIPTION OF THE INVENTION

Figure 1:
FIG. 1 is a light micrograph (magnification ×2500) of a pod inside a gill flap isolated from *Limulus polyohemus*, with forming amebocytes on the right end (cells with dark inclusions).

The amebocyte blood cells of the horseshoe crab, *Limulus polyphemus, Tachypleus tridentatus, Tachypleus gigas*, and *Carcinoscorpius rotundicauda* can be harvested, ruptured with distilled water, and freeze-dried, to produce a product that is, upon reconstitution, exquisitely sensitive to the presence of bacterial endotoxins. Limulus Amebocyte Lysate, or LAL, is used as a quantifiable and reliable test for the presence of contamination by Gram-negative bacteria, and is approved by the FDA for the testing of foods, dialysis machines, surgical instruments, injectable drugs, etc. LAL testing is important because even "sterile" equipment or drugs can carry these compounds, which may cause high fever and death when present in the bloodstream in even minute amounts. FDA regulations prohibit the killing of horseshoe crabs to produce this product, and each bled crab must be returned to its site of collection within 72 hours. Nevertheless, some of the animals do die. Many more are killed for bait by the unregulated conch and eel fishing industry, so that large crabs for bleeding are often in short supply, even in summer, which is the only time they come inshore and can be easily collected.

The present invention arises from the discovery that the source of the amebocytes in horseshoe crabs, especially *Limulus polyphemus*, are the gill flaps, flat, very thin, double membrane structures used in oxygen exchange by the animal. More than a thousand gill flaps are present on either side of the undercarriage of the horseshoe crab. Approximately one hundred flaps can be removed without harming the animal.

Even though others have long been aware of the function of the gill flaps in gas exchange, and have even excised the gill flaps for studies on the mobility of amebocytes, it was not previously known that these appendages were the source of the amebocytes. It has now been discovered that the horseshoe crab produces amebocytes 10 from gill flap tissue 11, collected in "pods" 12, located within the gill flap leaflets 14, as shown in FIG. 1.

The method of the present invention includes the steps of excising the gill flaps from the horseshoe crab, disinfecting the flaps, opening the flaps along one edge using an instrument such as a needle, and culturing the amebocyte-producing tissue in a nutrient solution, either directly on the opened gill flap leaflets or on a biocompatible support material such as a collagen or fibronectin sheet or polystyrene microspheres. The tissue is then grown in culture medium where it produces large numbers of competent amebocytes that do not leave the flap unless rinsed in a solution such as Limulus serum, detergent or copper sulfate. Shaking of the gill flap tissue in these solutions for less than a day releases the amebocytes for further culture; longer shaking dislodges the "pods" as well, and decreases efficiency of the culture. The gill flaps continue to produce amebocytes for periods in excess of six weeks, even after amebocytes are removed by pulsing for short periods with serum, detergent, or a copper sulfate solution.

The released amebocytes are washed and lysed using methods known to those skilled in the art to prepare lysate from amebocytes isolated from the blood of captured horseshoe crabs. For example, the cells can be ruptured by placing in distilled water, the cell debris removed by centrifugation or filtration, and the lysate lyophilized. The lysate is redissolved in deionized water to a concentration which is sensitive to a particular quantity of endotoxin, for example, 0.125 EU/ml. ("EU" stands for Endotoxin Units). Lysate must be sensitive to as little as 1 ng endotoxin to be considered acceptable.

At this time, the preferred procedure is as follows:
1. Remove gill flaps from adult horseshoe crab (up to 100 may be taken without ill effects) and place in Alcide Exspor fixative (4 parts water, 1 part disinfectant base, 1 part activator) Alcide Corp, Norwalk, Conn. for a period sufficient to disinfect the gill flaps, generally about 15 minutes. This disinfects and makes the flaps easier to open.
2. Working in a sterile laminar flow hood, slip and twist a glass needle between the two layers of the gill flap to open. The needles are preferably micropipettes pulled from 1.0 mm diameter borosilicate glass tubing on a horizontal microelectrode puller (World Precision Instruments PUL-1). Glass must be previously rendered pyrogen-free by baking at 400° F. dry heat for 4 hours. After the needle is inserted into the flap, it can be forced to the border opposite the cut edge and drawn from one end to the other to separate the two sides of the flap from each other, using great care. The opened gill flap is placed in incubation medium, preferably Grace's Insect Medium at pH 7.6 containing 500 μg streptomycin, 500 I.U. penicillin per ml, five times the normal amount, for several minutes. Bare hands may be used if well scrubbed and disinfected with 70% ethanol.

3. Transfer gill flap halves to culture tubes, flasks, or other containers, containing normal antibiotics, 100 μg streptomycin, 100 I.U. penicillin per ml, and 1% Tween 80 detergent, to prevent clumping, and incubate on a shaker table for 5 to 12 days, preferably at room temperature. The temperature can vary from 23°–37° C. The temperature of 26° C. is the most preferred. During this time new amebocytes, recognizable by their small size, 5 μm diameter, will be produced, which will adhere to the gill flap and not be released into the culture medium.

4. Release amebocytes by pulsing with a solution of 10 to 20% Limulus serum, preferably containing no anticoagulants. A commercial source of serum is Endosafe, Inc., Charleston, S.C. Medium containing amebocytes can now be drawn off and cultured to maturity. Gill flap tissue, replenished with serum-free medium, will continue to produce amebocytes and amebocytes can be harvested by repeated flushing of growing amebocytes from these flaps by pulses of Limulus blood serum, detergent (Tween 80), a copper sulfate solution or a combination thereof, every 10 to 20 days of the culturing process. The gill leaflets can remain in modified Grace's plus serum for up to seven days before the pods fall off. In the presence of serum, the pods fall off, and, after seven days, begin to deteriorate. Once removed from the gill flaps, deterioration of the pods begins sooner if not in the presence of serum. Gill flap tissue can also be cultured in modified Grace's media without serum, for example, seawater containing Gibco's Essential and Nonessential amino acids and Vitamins, buffered with HEPES buffer.

The method and means of the present invention are further illustrated by the following non-limiting example of the isolation of amebocyte-producing tissue from gill flaps and preparation of lysate.

Twenty-four hours before procedure:

Pull approximately 12 glass needles from capillary tubes (World Precision Instrument, Inc., Glass 1BBL W/Fil 1.0 mm 4 IN, 1 B100F-4) on the World Precision Instrument PUL-1. Place the glass needles in a glass petri dish and wrap with aluminum foil. Put the wrapped petri dish in a drying oven set at 100°–180° C. overnight, preferably 180° C.

Procedure:

1. Prepare a mixture of Alcide Brand Exspor 1:1:4 (1 part base—1 part activator—4 parts tap water) for sterilization of the external gill flap.

2. Sterilize scissors in the prepared Alcide mixture before removing the gill flaps from the crab. Remove the larger leaflets, closer to the body of the crab as opposed to the tail end. Cut close to the body when removing the gill leaflet and immediately place the gills into the Alcide. Spread the leaflets over the surface to provide maximum surface sterilization. Leave gill leaflets in Alcide mixture for approximately 15 minutes.

3. Make up a solution of media (Grace's Insect Medium, Dry: Cat. #56-902-101, Hazelton Research Products, Inc., 13804 W. 107th St., Lenexa, Kans. 66215 or Liquid: Cat. #350-1590, Gibco Laboratories, Grand Island, N.Y. 14072; using 10 mM HEPES buffer, Cat #380-5630 AG, Gibco Labs., to adjust pH to between 6.4–8.3, preferably 7.4–7.6, most preferably 7.56 with NaOH or HCl; with 5× antibiotics add 20 ml/liter of Penicillin/Streptomycin to a final concentration of 100 I.U. Penicillin/100 μg strep/ml Cat. #NCC-316, DuPont NEN Research Products, Boston, Mass.; 19.6 g Hank's balanced salts solution/l, Sigma; and Tween 80 (Polyoxyethylene sorbitan monooleate), Sigma Chemical Co., P.O. Box 14508, St. Louis, Mo. 63178, Cat. #P1754, to 1%).

4. Wash the Alcide sterilized gill leaflets: Place 20 ml of the modified Grace's medium plus six ml additional penicillin/streptomycin stock solution in a petri dish under a laminar flow hood. Wash each leaflet in the petri dish and place it in a second petri dish with the same mixture until ready to open.

5. Under a hood, mix 4 ml modified Grace's medium and 1 ml Limulus serum collected without anticoagulants, available from Endosafe, Inc., Charleston, S.C. Add 2.5 ml inoculum and 20 ml Grace's modified medium to 50 ml centrifuge tubes for culturing the amebocytes. A 50 ml centrifuge tube will hold 20 ml Grace's modified medium plus 2.5 ml inoculum.

6. Using sterile conditions, carefully insert the tip of a glass needle from the petri dish left overnight in the drying oven into the cut end of a gill leaflet. Push needle into the bristled border of the gill flap and move the needle to the upper end of the leaflet. Then, carefully move needle down the leaflet end to end. Keep the needle inside and move the needle to the center of the leaflet. Trim all the bristled border off the gill with scissors flamed in 90% ethanol. Next, push the needle through the gill leaflet. Peel open the gill leaflet into the two halves.

7. Place both halves into the same centrifuge tube using the glass needle. Flame, close the cover and tip the tube to cover the gill leaflets with medium. Parafilm the cover and put the tube in a shaker on its side and incubate at 26° C. The medium must move from side to side. The shaker is set at a speed of between approximately 50 rpm to 200 rpm, preferably 103 rpm. Any orbital shaker, e.g., Lab-Line Junior Orbit Shaker Lab-Line Instruments, Melrose Park, Ill., can be used. centrifuge tube can be left in the shaker for up to five days. After the gill leaflet is opened, both halves are put into a 50 ml centrifuge tube containing 20 ml of media (modified Grace's as described above without serum). Put in shaker lying flat with solution moving the length of the tube. After 2–5 days, add 1–2 ml of Limulus serum. Amebocytes will release from the leaflet. Remove and resuspend the emptied leaflet into 20 ml modified Grace's. The gill leaflet will become repopulated with amebocytes.

8. Optionally, inoculate 2.5 ml of the pods and loose amebocytes into a 50 ml centrifuge tube containing 20 ml of modified Grace's medium. Within three days, the culture becomes cloudy with amebocytes and absorbance readings 550 mm double.

In still another variation, ten or more opened gill flaps (both sides) are placed in a pyrogen-free (baked at 250° C. for 30 min or 180° C. for 3 hr) 500 ml beaker, with a heat-depyrogenated teflon-coated stir bar, and 400 ml of medium added. The beaker is covered with parafilm, and placed on a magnetic stirrer at low speed (5–80 rpm). Add 20% Limulus serum, or an equivalent, every four days, to flush amebocytes from flaps. Change medium to harvest cells every 5 days. This procedure can be varied and optimized as described below and using methods known to those skilled in the art.

In a manner analogous to the stimulation of proliferation of amebocytes, which occurs following exposure of horseshoe crabs to contamination, especially very low levels of endotoxin, it is possible to manipulate production of amebocytes and the amount of lysate proteins produced intracellularly. The amount of endotoxin or contamination must be small enough not to cause degranulation. The amebocytes in the medium are preferably allowed to mature for 15-20 days in a shaker, 103 rpm at 26° C. Serum is added to hasten the release of the amebocytes on the leaflet. In a variation of the method described in the example, the inoculum is placed in a culture flask treated with one of the following surface coatings:

A. Poly-d-Lysine [Hydrobromide] Sigma Cell Culture Reagents, Product No. P7405, applied using the procedure for covering the surface in the directions from Sigma to a thickness of 5.0 $\mu g/cm^2$.

B. Collagen type I, applied using the protocol in Animal Culture, Freshney, R. I., pages 29-30 (IRL Press, Oxford, Washington, D.C. 1986).

C. Fibronectin, applied according to the directions of the manufacturer, for example, BRL, Bethesda Research Laboratories, Collaborative Research, Beford, Mass., or Gibco, Grand Island, N.Y.

D. Microcarriers: for example, as manufactured by Nunc-Biosilon TM, Polystyrene, Spherical, 160-300 $\mu m$ diameter, 255 $cm^2$/ surface area, dry sterile; or Lux, Cytosphere TM, Polystyrene, Spherical, size 160-300 $\mu m$ diameter, 225 $cm^2/g$ surface area, Dry sterile, The microcarrier beads can be placed in a batch or rolling bottle fermentor where the tissues are able to produce amebocytes, or the process can be extended into a serial fermentor, including a final stage that produces lysate.

Stage One: tissues produce amebocytes, amebocytes released into the media.

Stage Two: media and amebocytes drained into second tank to mature.

Stage Three: amebocytes lysed, impurities removed.

Alternatively, pods can be placed in a fermentor without a carrier, using a filter system to isolate the amebocytes and exchange the media, leaving behind the tissues.

Since amebocyte production will decline with time and non-replenishing of media, a batch system can be designed to grow amebocytes in a single tank, where the media is replenished after the pods disappear and the amebocytes allowed to mature, then lysed.

Modifications an variations of the present invention will be obvious to those skilled in the art from the foregoing detailed description of the invention. Such modifications and variations are intended to come within the scope of the appended claims.

We claim:

1. A method for producing a horseshoe crab lysate comprising:
providing excised gill flap tissues from a horseshoe crab selected from the group consisting of *Limulus polyphemus, Tachypleus tridentatus, Tachypleus gigas,* and *Carcinoscorpius rotundicauda,*
opening the gill flap tissues,
culturing the gill flap tissues in a culture medium,
harvesting the amebocytes, and
lysing the amebocytes.

2. The method of claim 1 wherein the tissues are pods contained within the gill flaps and the pods are separated from the gill flaps prior to culturing.

3. The method of claim 1 wherein the amebocytes are harvested by releasing the amebocytes from the gill flaps by exposing the gill flap tissue to a solution selected from the group consisting of between approximately 10 and 20% Limulus serum, a detergent solution, copper sulfate solutions and combinations thereof.

4. The method of claim 1 further comprising exposing the gill flap tissue to low levels of endotoxin prior to harvesting the amebocytes.

* * * * *